(12) United States Patent
Rubin et al.

(10) Patent No.: US 6,261,997 B1
(45) Date of Patent: Jul. 17, 2001

(54) SLOW RELEASE FORMULATIONS OF PESTICIDES

(75) Inventors: Baruch Rubin, Maskarat Batya; Yasser El-Nahhal, Gaza; Shlomo Nir, Maskarat Batya; Leon Margulies, deceased, late of Rehovot, all of (IL), by Julia Margulies, heiress

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/261,484

(22) Filed: Mar. 1, 1999

Related U.S. Application Data

(63) Continuation-in-part of application No. PCT/IL97/00277, filed on Aug. 18, 1997.

(30) Foreign Application Priority Data

Aug. 28, 1996 (IL) ........................................ 119142

(51) Int. Cl.⁷ .......................... A01N 33/00; A01N 37/18; A01N 37/22; A61K 39/42
(52) U.S. Cl. .......................... 504/148; 504/340; 504/341; 504/342; 424/405
(58) Field of Search .................................. 504/326, 340, 504/341, 342, 148; 424/405

(56) References Cited

U.S. PATENT DOCUMENTS

| 4,386,010 | | 5/1983 | Hildebrandt | 252/428 |
| 4,695,511 | * | 9/1987 | Goodman et al. | 428/404 |
| 5,237,945 | | 8/1993 | White | 112/420 |
| 5,401,418 | * | 3/1995 | Boyd | 210/691 |

FOREIGN PATENT DOCUMENTS

| 559587 | 4/1985 | (AU) . |
| 5085902 | 4/1993 | (JP) . |
| 7291805 | 11/1995 | (JP) . |

* cited by examiner

*Primary Examiner*—S. Mark Clardy
*Assistant Examiner*—Alton Pryor
(74) *Attorney, Agent, or Firm*—Eitan, Pearl, Latzer & Cohen-Zedek

(57) ABSTRACT

Slow-Release agrochemical formulations for the prevention of leaching and contamination of soil and ground water, are described. The agrochemicals are organic compounds with non-ionic and non polar molecular structures, which are adsorbed to clays whose surface properties have been transformed from hydrophilic to hydrophobic by previous adsorption of an organic cation, usually of quaternary ammonium structure, having at least one aryl group attached to the ammonium nitrogen atom. The intermolecular interactions of the agrochemical with the organo-clay surface result in a reduction of its leaching in the field.

19 Claims, 3 Drawing Sheets

SLOW RELEASE FORMULATIONS OF PESTICIDES

CROSS-REFERENCE TO RELATED APPLICATIONS

This application is a Continuation-In-Part Application of International Patent Application Number PCT/IL97/00277 filed on Aug. 18, 1997, which corresponds to the international publication WO 98/08380.

FIELD OF INVENTION

The present invention relates to slow release of pesticide formulations designated for the prevention of teaching and contamination of soil and ground water. The pesticides to which this invention can be applied are organic compounds with non-ionic and non-polar molecular structures. These are adsorbed to clays whose surface properties have been transformed from hydrophilic to hydrophobic by previous adsorption of an organic cation, usually of quaternary ammonium structure having at least one benzyl group attached to the ammonium nitrogen atom. These groups are suitable adsorption sites of the organoclay for the pesticide molecules, and the intermolecular interactions on the clay surface result in reduction of the solubility in water of the active compounds, preventing its leaching in the field.

BACKGROUND OF THE INVENTION

The increasing use of pesticides such as herbicides, fungicides, insecticides, etc., poses serious health and environmental problems which must be controlled in order to minimize the harmful effects of those products. One problem frequently encountered with herbicides, such as alachlor, metolachlor, acetochlor, norflurazon and sulfometuron is leaching and migration, which results in loss of herbicidal efficiency and can cause damage to other crops and contaminate water. Alachlor and metolachlor have already been detected in ground water (Yaron et al., 1984, Garner et al., 1986). Thus, only a small fraction of the pesticides applied has desired activity. This imposes repeated applications and increasing cost and ecological damage. It is therefore highly desirable to develop methods which would prevent leaching and migration of pesticides from the top layers of soils, while still maintaining the biological activity in those layers. Ground water contamination by alachlor has been reported in several states of the USA and Canada (Chesters G. et al, 1989; Minnesota Environmental Quality Board, 1988). In most cases alachlor contamination of ground water has been attributed to point source contamination that resulted from improper handling, spills, and leaks (Hung and Frink 1989). However agriculture has been implicated as the non-point source of ground water contamination (Goodrich et al 1991). The downward transport of alachlor to the ground water is controlled primarily by retention and transportation processes. Occurrences of surface and ground water contamination by pesticides including alachlor and metolachlor have been revealed by monitoring programs (Chesters G. et al 1989). Alachlor residues in raw water intakes and tap water is evident (USEPA 1986). Recent monitoring programs show increasing numbers of pesticides in ground water. Cohen et al 1986 reported 17 pesticides in ground water in 23 States of the USA as a result of agricultural practices.

Ground water contamination resulting from the use of alachlor and metolachlor and other herbicides is affected by soil texture, organic matter content, depth to the ground water, temperature, relative humidity, precipitation and irrigation and the amount of herbicide applied. Recent studies on the distribution and dissipation of metolachlor in soil columns (Zheng et al 1993) have shown that the rate of herbicide migration increased with larger doses. Results of this study show that 84–91% of the applied metolachlor was found in the superficial layer (0–9 cm) three days after application, 28 and 56 days after treatment, metolachlor was observed at 21–27 and 27–33 cm depth, respectively. This depth of migration seems more important than described by Bowman (1988, 1989) who reported that metolachlor moved down no more than 10 cm.

As indicated above, the use of available herbicide formulations poses a serious problem of soil and ground water contamination. Such available formulations include soluble concentrate (SC) and emulsion concentrate (EC). Sometimes SC are prepared from chemically modified herbicides whose molecular structure is changed by introducing polar or ionic substituent that increase the solubility in water. This results in an increased leaching in soils. An EC formulation of alachlor has been prepared by the mixing from about 20.0 to about 35.0 percent by weight of alachlor, from about 1.25 to about 1.75 percent by weight of organophylic clay, from about 4.5 to about 9.0 percent by weight of an emulsifier selected from the group consisting of alkyl aryl sulfonates, phosphate esters of nonyl phenol ethoxylates and polyalkyleneglycol ether; from about 10.0 to about 20.0 percentage by weight of an organic solvent in which the herbicide is soluble, which is non reactive to the said herbicide and which is essentially water-soluble, balancing being made up of water (Prill, Erhard J Kirkwood; U.S. Pat. No. 4,440,562).

Another attempt involved a herbicide in fluid suspension consisting of alachlor and chloralkylamino triazine based stabilized product (Arion D; Dorin E; Dragusin E; Katona N; Macaric G; Roibu C; Sarpe N; and Staicu S Rumanian Patent Number RO 137906(890126)). In this attempt the herbicide comprises a 1:1 to 2:1 synergetic ratio alachlor chloralkylamino-s-triazine active substance mix with 20–40% of toluene or xylene as stabilizer and 8–12% mixture of calcium alkyl aryl sulphonate and e.g., polyethoxylated castor oil, 0.5–1.5% of montmorillonitic clay, 1.0–2.5% of ethylene glycol, 0.2–2% of magnesium oxide, blacidic potassium phosphate and borax, remainder water up to 100%. The above mentioned patent was an attempt to improve the herbicidal activity of the herbicide, but ignored the importance of preventing leaching and protecting the groundwater from the contamination by herbicides.

Modification of pesticide behavior by encapsulating the chemicals in a starch matrix is one experimental approach receiving, increased attention (Wing et al 1987). Starch encapsulation has been shown to reduce volatilization (Schreiber et al 1987) and leaching (Gish et al 1991) losses of some herbicides, in this attempt it was found that water potential, imposed using polyethylene glycol, significantly influenced the swelling of the starch matrix and rate of release of both alachlor and atrazine. At 0 MPa water potential complete release requires 21 days for atrazine and 7 days for alachlor. As water potential declined, so did the rate of release (Wienhood and Gish 1992). Results of this work showed that water potential exerts a significant effect on the rate of herbicidal release. It is clear that the ground water is not protected by the use of these encapsulations because the herbicide will be released from the microcapsules and it will leach for certain amounts of water applied. Therefore, this encapsulation approach in a pesticide formulation is not effective in preventing leaching and protecting ground water and soil from herbicide contamination.

Recently, the use of an organo ammonium substituted smectite clay was suggested for controlled release.

(Knudson, Jr, Milburn I Gonzales, U.S. Pat. No. 4,849,006). In this attempt controlled release composition is prepared by contacting an organoclay with a biologically active material in concentrated form to cause absorption of the active material in the organoclay. This patent deals with slow release of volatile herbicides to the open atmosphere and does not mention the problem of leaching in soil. In this patent the organoclay is a C12–C18 dialkyl dimethyl ammonium organoclay, or a benzyl ammonium organoclay or a hydroxyalkyl ammonium organoclay. Other organoclays suggested include montmorillonite modified by ammonium cation containing the following four groups: a) C4–C24 alkyl, b) hydrogen, c) benzyl or C4–C24 alkyl, d) hydrogen or C1–C4 alkyl.

It was found that the compounds of this patent do not give satisfactory results.

SUMMARY OF THE INVENTION

The present invention relates to slow release agrochemical formulations, such as pesticides which substantially reduce leaching of the active ingredient into ground water.

There is thus provided experimental evidence that pesticides adsorbed on organoclays (OC) help in preventing the contamination of underground an surface water by pesticides.

As opposed to the emulsion formulation described in the prior art, which is mobile throughout the soil profile, in the organoclay formulations of the present invention, the herbicidal activity is retained in the top soil (0–10 cm).

As opposed to the encapsulations described in the prior art, in the organoclay formulations of the present invention, the prevention of leaching in the soil was observed even for a large amount of water applied (up to 1000 m3/ha).

The organoclay formulations according to the present invention comprise as a carrier a clay, the surface properties of which have been modified from hydrophilic to hydrophobic or partially hydrophobic by adsorption of a quaternary ammonium moiety, preferably having at least one aryl group attached to the ammonium nitrogen atom to which there is attached the active agrochemical.

DETAILED DESCRIPTION OF THE INVENTION

Figure 1A:
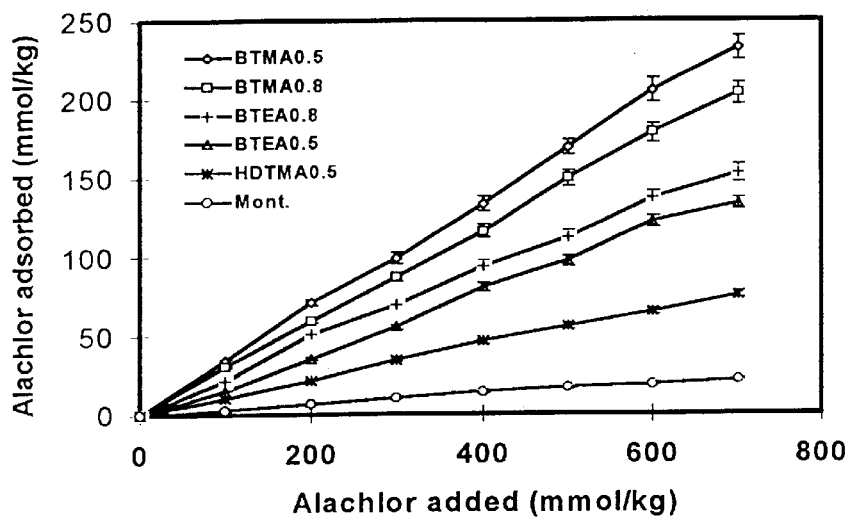
FIGS. 1A and 1B are graphic presentations of the results of adsorption of alachlor and acetochlor, respectively on montmorillonite pre adsorbed by several organic cations.

The present invention is exemplified with reference to certain specific herbicides, but the invention is described in the following, by way of illustration, with reference to some very well known and widely used herbicides.

It ought to be understood that this description is by way of illustration only and that the invention is applicable to a wide variety of agrochemical compounds which have similar physical properties, allowing the surface treatment of the carrier and subsequent bonding of the agrochemical.

The experimental tests included a formulation of alachlor adsorbed on montmorillonite modified by the adsorption of the organic cation Hexadecyl trimethyl ammonium (HDTMA) that has one C16 alkyl chain of three C1 methyl groups. The results of the laboratory and field experiments show that such an organoclay does not inhibit the movement of the herbicide in the soil profile. It can be concluded that the C16 alkyl group does not contribute to the adsorption of the herbicides having an aromatic ring structure, but has rather a steric hindrance effect. For those cases, the presence of a benzyl group and only C1–C4 substituents in the ammonium cation are necessary.

It was found that the best results are obtained when the clay modifying agents are phenyltrimethyl ammonium (PTMA) benzyltrimethyl ammonium chloride (BTMA), benzyltriethyl ammonium bromide (BTEA) or benzyl tributyl ammonium chloride (BTBA). In these cases significant inhibition of herbicide leaching has been achieved. The same trend was also found for norflurazon and acetochlor. It was deduced that the enhanced adsorbed amounts at ⅝ of the CEC for such herbicides are mainly due to interactions between the phenyl rings of herbicide molecules and organic cations, which are favored for the smaller cations. In line with this trend, the use of the organic cation phenyltrimethylammonium (PTMA), which is smaller than BTMA, gave the best formulation of metolachlor in terms of reduced leaching. Adsorption affinity paralleled reduction of leaching. Enhanced adsorption of acetochlor was found when montmorillonite was preadsorbed by PTMA 0.5 mmol/g clay.

EXPERIMENTAL a. Preparation of the formulations

The main idea behind the suggested method of stabilizing leachable non polar pesticides is to adsorb them on clays whose surface change has been partially or totally neutralized by suitable organic ammonium cations.

A suitable concentrated solution of the organic cation is added dropwise to a 0.5 or 1% W/W of clay suspension (e.g. Montmorillonite; Sepiolite; Palygorskite; Pillared clays). After separation of the supernatant, the organoclay complex is dried and ground to less than 50 μm. The herbicide is dissolved in a suitable volatile organic solvent e.g. hexane, dichloro methane, acetone, and mixed with the solid organoclay in weight relations of 5–20 g of herbicide to 95–80 g organoclay. The organic solvent is evaporated under gentle reduced pressure and continuous mixing and the resulting herbicide-organoclay complex is ground to less than 50 μm. The pesticide formulation can be further improved by adding water or another solvent to the dried material; removing the loosely bound pesticide, and drying again. The results described in FIGS. 1A and 1B show the enhanced adsorption of alachlor (FIG. 1A) and acetochlor (FIG. 1B) on montmorillonite pre adsorbed by several organic cations.

FIG. 1A shows adsorption isotherms of alachlor on montmorillonite alone (Mont), montmorillonite pre-adsorbed with either BTMA 0.5 mole/kg. BTMS 0.8 mole/kg, BTEA 0.8 mole/kg, BTEA 0.5 mole/kg or HDTMA 0.5 mole/kg clay. Bars indicate standard errors.

Figure 1B:
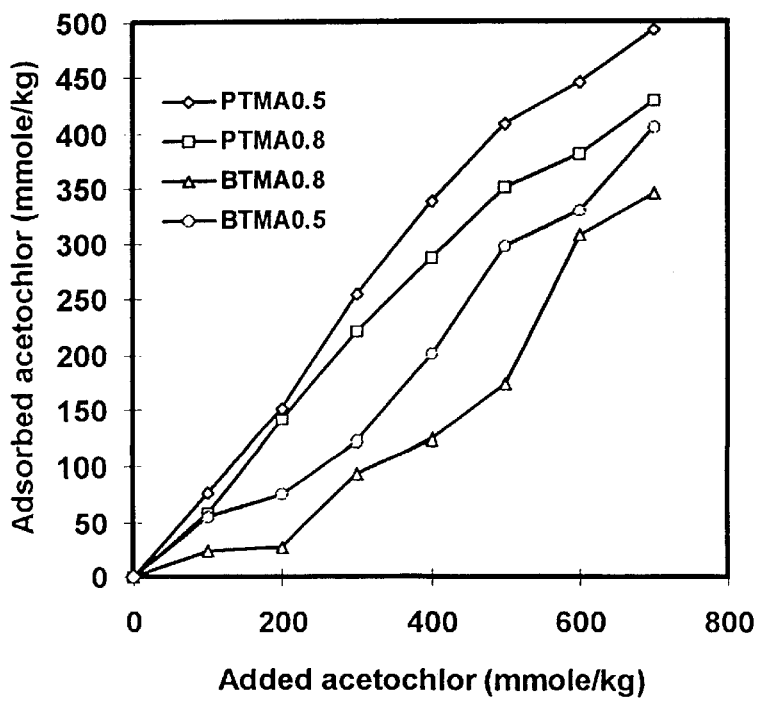

FIG. 1B shows adsorption isotherms of acetochlor on montmorillonite pre-adsorbed with either PTMA or BTMA at a loading of 0.5 or 0.8 mole/kg clay.

b. leaching studies and bioassays

1. Under laboratory and field conditions, the following bioassay column technique was used to evaluate the leaching of the herbicide using sensitive plants to the given herbicide. Briefly, the experiments have used 100×100×200 mm tin columns filled with soil. The column surface is sprayed with either the commercial formulation of the herbicide or with the organoclay formulated herbicide. The herbicide is added at the same amounts as in the field applications, i.e., 200 g of the active ingredient per 1000 m². Then the columns are irrigated with 50 m³/1000 m³. The water is added throughout 5 hours. The columns are left for 24 hr and then sliced along their lengths into two parts (right and left). Two plants, setaria and wheat were sown in each part in two rows and irrigated with water. The height and the weight of the plants 7 days after emergence are used as an indicator of the presence of herbicide at different depths in the soil column.

2. Under field conditions the soil samples are sprayed with the organoclay-formulated herbicide along with the EC commercial formulation for comparison purposes, using the same field rate. The treated soils are irrigated at the same field rate (50 cubic meter/1000 m²). Soil samples are taken from different soil depths for the bioassay techniques as described above. Inhibition of the growth is taken as an indicator of the presence of the herbicide at the soil depth.

Figure 2:
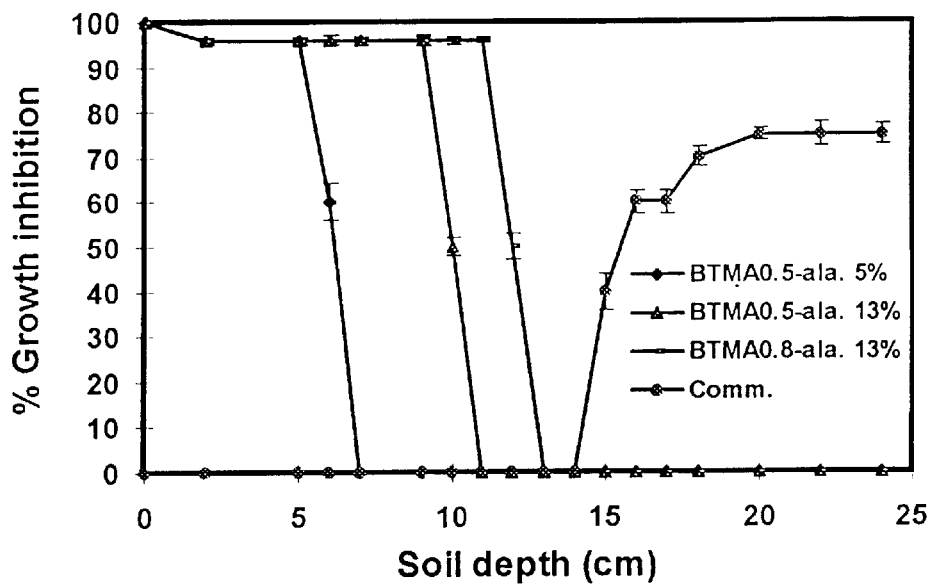
FIGS. 2 and 3 are graphic presentations showing the effect of different loads of alachlor and BTMA adsorbed on clay, on leaching in the laboratory and under field conditions, respectively.

FIG. 2 shows the effect of different loads of alachlor and BTMA adsorbed on clay on leaching of alachlor using sandy soil columns, and green foxtail as a test plant. Alachlor was applied at 2.0 kg/ha followed by irrigation of 500 m³/ha. bars indicate standard errors.

Figure 3:
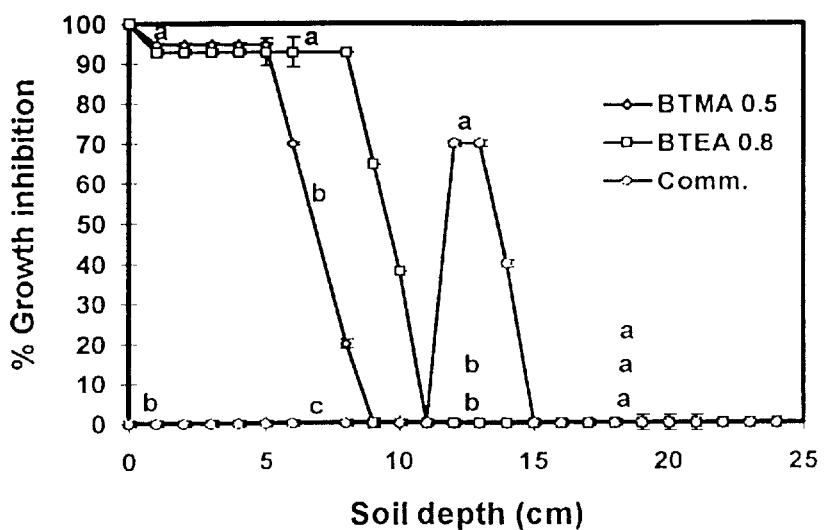

FIG. 3 shows leaching of commercial formulation of alachlor (comm.), Mont-BTMA 0.5 and Mont-BTEA 0.8 mmole/g clay containing alachlor 13% under field conditions using green foxtail as a test plant. Alachlor was applied at 2.0 kg/ha followed by irrigation of 500 m³/ha. Means followed by the same letter at a representative depth are not significantly different at $\alpha=0.05$ level. Bars indicate standard errors.

Results presented in Table 1 show that for the commercial formulation of alachlor, the herbicidal activity disappears from the top soil, being leached to below 13 cm depth under the laboratory conditions (FIG. 2), and to 12 cm under field conditions (FIG. 3). On the other hand, in the organoclay formulation, the herbicidal activity of alachlor is fully maintained in the top 10 cm under laboratory conditions and down to 8 cm under field conditions. Similar results are observed using the BTEA organic cation in the organoclay formulation (Table 2).

Table 3 shows that the herbicidal activity of metolachlor is retained using a BTEA-montmorillonite formulation in the top 8–12 cm depth, whereas the commercial formulation leached down to more than 20 cm depth.

Figure 4:
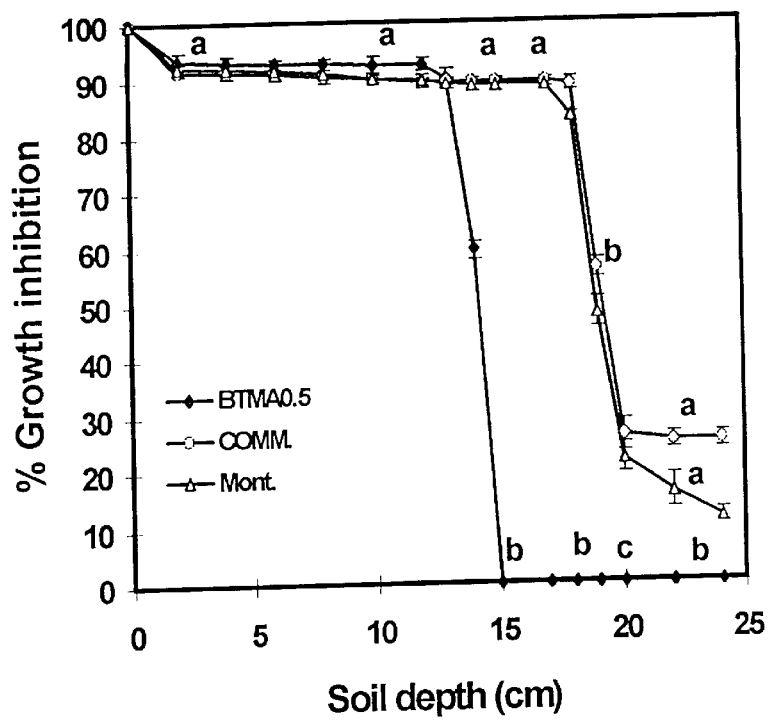
FIGS. 4 and 5 are graphic presentations showing the leaching of different formulas of metolachlor.

FIG. 4 shows leaching of different formulations of metolachlor (2.0 kg/ha) in columns filled with sandy soil following irrigation with 500 m³/ha. Green foxtail growth was used to estimate the presence of matolachlor. Metolachlor formulations were commercial formulation (comm.); metolachlor on clay alone (Mont); metolachlor on clay pre-absorbed with BTMA 0.5 mole/kg clay. The clay based formulations contained 13% metolachlor. Means followed by the same letter at a representative depth are not significantly different at $\rho=0.05$ level. Bars indicate standard errors.

Figure 5:
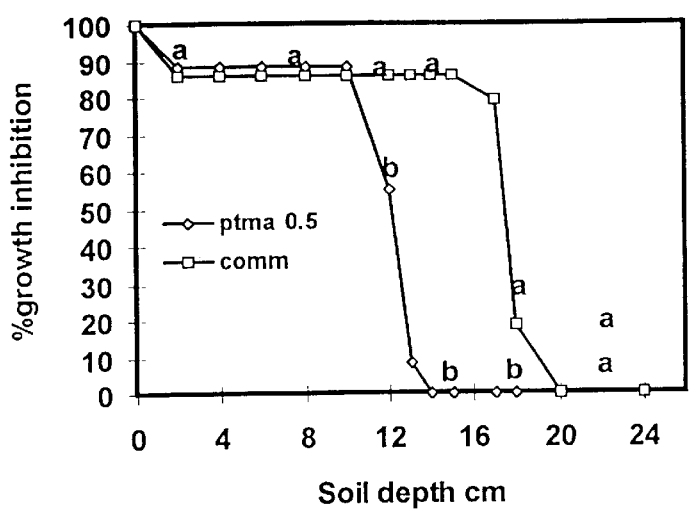

FIG. 5 shows leaching of different formulations of metolachlor (2.0 kg/ha) in columns filled with sandy soil following irrigation with 500 m³/ha. Green foxtail growth was used to estimate the presence of matolachlor. Metolachlor formulations were commercial formulation (comm.); metolachlor on clay pre-absorbed with PTMA 0.5 mole/kg clay. The clay based formulations contained 13% metolachlor. Means followed by the same letter at a representative depth are not significantly different at $\rho=0.05$ level. Bars indicate standard errors.

FIGS. 4 and 5 show that the herbicidal activity of metolachlor is retained using BTMA or PTMA—montmorillonite formulation in the top 8 12 cm depth, whereas the commercial formulation leached down to more than 20 cm depth. PTMA (phenyltrimethylammonium) is a smaller organic cation than BTMA.

The use of treated organoclays in the alachlor and metolachlor formulations, inhibits considerably the leaching of the herbicides both under laboratory and under field conditions.

In a similar manner the above principles can be applied to other herbicides such as acetochlor, butachlor, norflurazon, sulfometuron, atrazine; to insecticides such as Azinphos, 2-sec-buthylphenyl methyl carbamate, carbaryl, carbofuran, chlordimeform, chlorfenvinphos, crotoxyphos, ethiofencarb, fenamiphos, fensulfothion, formetanate, metolcarb, propoxur, tralomethrin, trichloronate; and to fungicides such as benalaxyl, benodanil, kitazin P, carboxin, ethirimol, fenitropan, fenpropimorph, furalaxyl, metalaxyl, oxycarboxin, pyracarbolid, tolyfluanid, triadimefon.

TABLE 1

Results of the leaching studies of alachlor commercial formulation and organoclay formulations under field and laboratory conditions. Values are given as % of inhibition of the control plants.

| Soil depth (cm) | commercial Alachlor (1) | commercial Alachlor (2) | BTMAO.5* Alachlor (1) | BTMAO.5* Alachlor (2) |
|---|---|---|---|---|
| 0 | 0 | 0 | 100 | 95 |
| 2 | 0 | 0 | 96 | 95 |
| 4 | 0 | 0 | 96 | 95 |
| 6 | 0 | 0 | 96 | 70 |
| 7 | 0 | 0 | 94 | 50 |
| 8 | 0 | 0 | 96 | 20 |
| 9 | 0 | 0 | 96 | 0 |
| 10 | 0 | 0 | 50 | 0 |
| 11 | 0 | 0 | 0 | 0 |
| 12 | 0 | 70 | 0 | 0 |
| 13 | 30 | 70 | 0 | 0 |
| 14 | 40 | 40 | 0 | 0 |
| 15 | 40 | 0 | 0 | 0 |
| 16 | 50 | 0 | 0 | 0 |
| 17 | 50 | 0 | 0 | 0 |
| 18 | 50 | 0 | 0 | 0 |
| 19 | 50 | 0 | 0 | 0 |
| 20 | 50 | 0 | 0 | 0 |
| 21 | 0 | 0 | 0 | 0 |
| 22 | 0 | 0 | 0 | 0 |
| 23 | 0 | 0 | 0 | 0 |
| 24 | 0 | 0 | 0 | 0 |

(1), (2) = Experiment was carried out under laboratory and field conditions, respectively.
*Organoclay formulation based on montmorillonite modified by BTMA (0.5 mmol BTMA per g clay), containing 13% w/w of alachlor.

TABLE 2

Results of the leaching studies of alachlor commercial formulation and organoclay formulations under field and laboratory conditions. Values are given as % of inhibition of the control plants.

| Soil depth (cm) | commercial Alachlor (1) | commercial Alachlor (2) | BTMAO.8* Alachlor (1) | BTMAO.8* Alachlor (2) |
|---|---|---|---|---|
| 0 | 0 | 0 | 100 | 100 |
| 2 | 0 | 0 | 94 | 92 |
| 4 | 0 | 0 | 94 | 92 |
| 6 | 0 | 0 | 94 | 92 |
| 7 | 0 | 0 | 94 | 92 |
| 8 | 0 | 0 | 53 | 50 |
| 9 | 0 | 0 | 20 | 0 |
| 10 | 30 | 0 | 0 | 0 |

TABLE 2-continued

Results of the leaching studies of alachlor commercial formulation and organoclay formulations under field and laboratory conditions. Values are given as % of inhibition of the control plants.

| Soil depth (cm) | commercial Alachlor (1) | commercial Alachlor (2) | BTMAO.8* Alachlor (1) | BTMAO.8* Alachlor (2) |
|---|---|---|---|---|
| 11 | 50 | 0  | 0  | 0 |
| 12 | 50 | 0  | 0  | 0 |
| 13 | 50 | 30 | 0  | 0 |
| 14 | 50 | 40 | 0  | 0 |
| 15 | 50 | 40 | 10 | 0 |
| 16 | 20 | 50 | 0  | 0 |
| 17 | 0  | 50 | 0  | 0 |
| 18 | 0  | 50 | 0  | 0 |
| 19 | 0  | 50 | 0  | 0 |
| 20 | 0  | 50 | 0  | 0 |
| 21 | 0  | 0  | 0  | 0 |
| 22 | 0  | 0  | 0  | 0 |
| 23 | 0  | 0  | 0  | 0 |
| 24 | 0  | 0  | 0  | 0 |
| 24 | 0  | 0  | 0  | 0 |

(1), (2) = Experiment was carried out under laboratory and field conditions, respectively.
*Organoclay formulation based on montmorillonite modified by BTMA (0.8 mmol BTMA per g clay), containing 13% w/w of alachlor.

TABLE 3

Results of the leaching studies of alachlor commercial formulation and organoclay formulations under field and laboratory conditions. Values are given as % of inhibition of the control plants.

| Soil depth (cm) | commercial Alachlor (1) | commercial Alachlor (2) | BTMAO.8* Alachlor (1) | BTMAO8* Alachlor (2) |
|---|---|---|---|---|
| 0  | 100 | 100 | 100 | 100 |
| 2  | 93  | 90  | 93  | 93 |
| 4  | 93  | 90  | 93  | 93 |
| 6  | 93  | 90  | 93  | 93 |
| 8  | 93  | 90  | 50  | 93 |
| 10 | 93  | 90  | 0   | 93 |
| 12 | 93  | 90  | 0   | 50 |
| 14 | 93  | 90  | 0   | 0 |
| 16 | 66  | 50  | 0   | 0 |
| 18 | 20  | 50  | 0   | 0 |
| 20 | 60  | 0   | 0   | 0 |
| 22 | 20  | 0   | 0   | 0 |
| 24 | 0   | 0   | 0   | 0 |

(1) = Experiment was carried out under laboratory conditions.
(2) = Experiment was carried out under field conditions.
*Organoclay formulation based on montmoillorite modified by BTMA (0.5 mmol BTMA per g clay), containing 13% w/w of metaclor.
*Commercial formulation as Emulsion Concentrate (EC)

REFERENCES

Arion, D., Dorin E., Dragusin E., Katona N., Macaric G., Marinica G., Roibu C., Sarpe N., and Staicu S. (Patent No. RO 137906(890126)). Herbicide in form of fluid suspension consists of alachlor and chloralkylamino triazine based stabilized product.

Bowman B. T. J. (1988). Environ. Qual. 1/:689–694.

Bowman B. T. J. (1989). Environ. Toxicol. and Chem. 8:485:491.

Chesters, G., Simsiman G. V., Levy J., Alhajjar B. J., Fathulla R. N., and Harkin J. M. (1989). Environmental fate of alachlor and metolachlor. Rev. Environ. Contm. Toxicol. 110: 1–74.

Cohen S Z, Eiden C, Lorben M N (1986). Monitoring ground water for pesticides. Am. Chem. Soc. Washington, D.C. pp 170–196.

Garner W. Y., Honeycut R. C., Nigg H., (1986) ACS Symposium Ser. 315, Washington, D.C. C)

Goodrich J. A., Lykine B. W. and Clark R. M. (1991). Drinking water from agriculturally contaminated groundwater. J. Environ. Qual. 20:707–717.

Gish T. J., Schoppet M. J., Helling C. S., Shirmohammadi A., Schreiber and Wing R. E. (1991). Transport comparison of technical grade and starch encapsulated atrazine. Trans. ASAE 34. 1738–1799.

Hung L. Q. and Frink C. R. (1989). Distribution of atrazin, simazine, alachlor and metolachlor in soil profiles in Connecticut. Bull. Environ. Contam. Toxicol. 43:159–164.

Prill, Erhard J Kirkwood M O. (U.S. Pat. No. 4,440,562). Herbicidal Emulsions, Isopropylamine salt of N phosphonomethylglycine, Alachlor clay surfactants.

Schreiber M. M., Shasha B. S. Ross M. A., Orwick P. L., and Edgecomb Jr. D. W. (1978). Efficacy and rate of release of EPTC and butylate from starch encapsulated formulation under greenhouse condition. Weed Sci. 26:679–686.

USEPA (1986) Alachlor. Special review technical support document. Position 2/3. Office of pesticides and toxic substance. U.S. Environmental Protection Agency Washington, D.C.

Wienhold J. B. and Gish T. J. (1992). Effect of water potential, temperature and soil microbial activity on release of starch encapsulated atrazine and alachlor. J. Environ. Qual. 21:382–386.

Wing R. E., Malti S. and Doane W. M. (1987) Effectiveness of jet-cooked pearl cornstarch as a controlled release matrix. Starch/Staerk 39:422–425.

Yaron B., Gerstel Z., and Spencer W. F., (1984). Adv. Soil Sc., 2-1-143.

Zheng S. Q., Cooper J. T., Fontanel P. V., Cost C. M., and Meat M. (1993). Distribution and dissipation of metolachlor in soil column. J. Environ. Sci. 6:641–653.

What is claimed is:

1. A slow release agrochemical composition comprising a clay mineral carrier with a surface rendered partially to fully hydrophobic by adsorption of a quaternary ammonium compound having at least one aryl substituent through which a pesticide is bonded.

2. A composition according to claim 1 where the quaternary ammonium is benzyltrimethyl ammonium chloride or bromide.

3. A composition according to claim 1 where the quaternary ammonium is benzyltriethyl ammonium chloride or bromide.

4. A composition according to claim 1 where the quaternary ammonium is phenyltrimethyl ammonium chloride or bromide.

5. A composition according to claim 3 where the clay mineral carrier is adsorbed by the quaternary ammonium up to about ⅝ of the cation exchange capacity of the clay mineral.

6. A composition according to claim 4 where the clay mineral carrier is adsorbed by the quaternary ammonium up to about ⅝ of the cation exchange capacity of the clay mineral.

7. A composition according to claim 1 where the clay mineral carrier is montmorillonite.

8. A composition according to claim 1 where the clay mineral carrier is of the tens of microns particle size.

9. A composition according to claim 7 where the pesticide is a herbicide.

10. A composition according to claim 9 where the herbicide is selected from alachlor, acetochlor and metolachlor.

11. A composition according to claim 1 where about 5 to 20 weight-% of the quaternary ammonium compound is attached to the clay mineral carrier.

12. A composition according to claim 1 where from about 5 weight-% to about 30 weight-% of the pesticide is attached to the clay mineral carrier.

13. A composition according to claim 1 where the pesticide is a non polar pesticide.

14. A method for the preparation of a slow release agrochemical composition that comprises a clay mineral carrier with a surface rendered partially to fully hydrophobic by adsorption of a quaternary ammonium compound having at least one aryl substituent through which an active compound is bonded, said method comprising the steps of adding a solution of said quaternary ammonium compound to a clay suspension;

separating said suspension to which the quaternary ammonium compound is selected is added, to a supernatant and an organoclay complex;

drying said organoclay complex;

adding a pesticide that is dissolved in an organic solvent, to the organoclay; and removing said organic solvent.

15. A method according to claim 14 further comprising the steps of adding a solvent to the dried organoclay complex removing loosely bound pesticide; and drying the resulting organoclay complex.

16. A method according to claim 14 where the clay suspension is at a concentration of 0.1–1% W/W.

17. A method according to claim 14 where the step of drying the organoclay complex is followed by a step of grinding the organoclay complex to particles of 50 $\mu$m or less.

18. A method according to claim 14 where the step of adding a pesticide that is dissolved in an organic solvent, to the organoclay includes adding 5–20 g of pesticide of 95–80 g organoclay.

19. A slow release agrochemical composition comprising a clay mineral carrier with a surface rendered partially hydrophobic by adsorption of a quaternary ammonium compound having at least one aryl substituent through which a pesticide is bonded.

* * * * *